United States Patent [19]

Sweeney et al.

[11] Patent Number: 5,057,637

[45] Date of Patent: Oct. 15, 1991

[54] PROCESS FOR PRODUCING $C_5$ TO $C_{18}$ STRAIGHT CHAIN α-OLEFINS FROM THE CORRESPONDING INTERNAL OLEFINS

[75] Inventors: William A. Sweeney, Larkspur; Gar L. Woo, Tiburon, both of Calif.

[73] Assignee: Chevron Research and Technology Company, San Francisco, Calif.

[21] Appl. No.: 542,387

[22] Filed: Jun. 22, 1990

[51] Int. Cl.$^5$ ............................................. C07C 1/00
[52] U.S. Cl. .................................. 585/324; 585/510; 585/520; 585/639; 585/643; 585/644; 585/648; 585/653
[58] Field of Search ............... 585/639, 648, 500, 324, 585/328, 510, 520, 643, 644, 653

[56] References Cited

U.S. PATENT DOCUMENTS

| | | | |
|---|---|---|---|
| 3,283,027 | 11/1966 | Lundeen et al. | 260/682 |
| 3,600,455 | 8/1971 | Dean | 260/682 |
| 4,234,752 | 11/1980 | Wa et al. | 585/640 |
| 4,270,015 | 5/1981 | Knifton | 585/324 |
| 4,490,567 | 12/1984 | Drake | 585/324 |

FOREIGN PATENT DOCUMENTS

| | | |
|---|---|---|
| 0222356 | 5/1987 | European Pat. Off. . |
| 0150832 | 2/1988 | European Pat. Off. . |
| 1233020 | 5/1971 | United Kingdom . |

OTHER PUBLICATIONS

Lundeen, et al., *JORG Chem*, vol. 32, 1967, pp. 3386-3389.

Davis, *American Chemical Society*, vol. 18, No. 3, 1979, pp. 191-198.

Che, et al., *Elsevier Science Publishers B.V.*, Amsterdam, 1985, pp. 309-318.

*Primary Examiner*—Curtis R. Davis
*Attorney, Agent, or Firm*—Richard J. Sheridan; Tom J. DeJonghe

[57] ABSTRACT

Disclosed is a process for preparing $C_5$ to $C_{18}$ straight chain α-olefins from the corresponding internal olefins. The process comprises reacting a $C_5$ $C_{18}$ straight chain olefin reactant with an electrophilic compound containing hydrogen followed by cracking the resulting product.

11 Claims, No Drawings

PROCESS FOR PRODUCING C₅ TO C₁₈ STRAIGHT CHAIN α-OLEFINS FROM THE CORRESPONDING INTERNAL OLEFINS

BACKGROUND OF THE INVENTION

1. Field of the Invention

The present invention relates to a method for producing $C_5$ to $C_{18}$ straight chain α-olefins from the corresponding internal olefin isomers.

2. Description of the Prior Art

Compounds having a terminal double bond (hereinafter referred to as "terminal olefins" or "α-olefins") are very useful industrially as raw materials for heat-resistant polymers, comonomers for the production of polyolefins, starting materials for detergents and so forth. The terminal olefin 1-hexene is especially valuable for many uses such as dimerization to dodecenes which are suitable for making biodegradable detergents, using it as a feed for the OXO reaction to make relatively linear $C_7$ alcohols, and as a comonomer in making linear low density polyethylene.

A potential source of 1-hexene is a mixture of n-hexenes which contains 1-hexene, cis and trans 2-hexene, and cis and trans 3-hexene. Unfortunately, however, the amount of 1-hexene in these mixtures is normally very low. For example, thermodynamic equilibration of n-hexenes produces a mixture containing only about 2-4% 1-hexene. While it is possible to separate the 1-hexene from the other n-hexenes in these mixtures, due to the very low levels of 1-hexene, such a procedure would be uneconomical. Thus, there exists a need for a method by which the amount of 1-hexene in these n-hexene mixtures can be substantially increased.

A known method for producing terminal olefins, such as 1-hexene, is to dehydrate a 2-alcohol, i.e., a compound of the formula

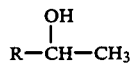

where R is a hydrocarbyl group. For example, U.S. Pat. No. 3,283,027, issued Nov. 1, 1966 to Lundeen et al., discloses the dehydration of 2-alcohols to terminal olefins using a catalyst which is a thorium, scandium, yttrium or rare earth oxide. While this dehydration reaction can produce an α-olefin and/or a 2-olefin, the Lundeen et al. product is said to be 90% or more α-olefin. U S. Pat. No. 3,600,455, issued Aug. 17, 1971 to Dean, discloses a process for producing the terminal olefin 4-methyl pentene-1 by dehydrating 4-methyl pentanol-1 or 4-methyl pentanol-2 by passing it over an alkalized alumina catalyst U.S. Pat. No. 4,234,752, issued Nov. 18, 1980 to Wu et al., discloses the dehydration of $C_{2-20}$ alcohols in the presence of gamma-alumina (which may be base-treated) employing an inert carrier gas to produce an olefin. The process is said to minimize isomerization which can convert desired products to undesired products. For example, according to Wu et al., 3-methyl-1-butanol can be dehydrated by this process to produce 3-methyl-1-butene having a 97.7 wt. % purity.

U.S. Pat. No. 4,490,567, issued Dec. 25, 1984 to Drake, discloses a process for the selective dehydration of 2-alcohols to α-olefins using a catalyst which is (1) at least one catalytic metal oxide on a low surface area aluminum oxide-containing support, or (2) a mixture of thorium oxide and cerium oxide on a base-treated aluminum oxide-containing support. Also described is a process for obtaining high purity 4-methyl-1-pentene by the dehydration of 4-methyl-2-pentanol followed by disproportionation with ethylene.

European Patent Specification Publication No. 0150832, published Nov. 2, 1988, discloses a process for preparing α-olefins by dehydrating 2-alcohols using a high purity (i.e., substantially free of silicon and titanium) zirconium oxide catalyst, and European Patent Specification Publication No. 0222356, published May 20, 1987, discloses the dehydration of 2-alcohols to α-olefins using a zirconia catalyst which has been treated with an alkaline solution.

Lundeen and Hoozer, "Selective Catalytic Dehydration. Thoria-Catalyzed Dehydration of Alcohols", J. Org, Chem., 32, pp. 3386–3389 (1967) discloses that the thoria-catalyzed dehydration of secondary 2-alcohols is selective for α-olefins, and that the amount of ketone by-product is low, and Davis, "Catalytic Conversion of Alcohols. 11. Influence of Preparation and Pretreatment on the Selectivity of Zirconia", Ind. Eng. Chem. Prod. Res. Dev., Vol. 18, No. 3, pp. 181–198 (1979) discloses that a zirconia catalyst is similar to thoria for both the dehydration and α-olefin selectivity in the conversion of 2-alcohols to olefins.

Other methods of preparing α-olefins are also known. For example, British Patent Specification No. 1,233,020, published May 26, 1971, discloses a method for making 4-methylpentene-1 by subjecting a mixture of acetone and isobutyraldehyde to conditions under which acetone undergoes condensation both with itself to form diacetone alcohol and with isobutyraldehyde to form the acetone/isobutyraldehyde condensate methyl 2-methyl 3-hydroxy butyl ketone, subjecting the mixed condensates to conditions under which they undergo dehydration to the corresponding olefinically unsaturated ketones, hydrogenating these ketones to saturated alcohols and dehydrating these saturated alcohols over alkalized alumina to form a mixture of 4-methylpentenes-1 and -2 and a mixture of methyl hexenes.

A process for producing $C_5$ to $C_{18}$ straight chain α-olefins from the corresponding internal olefins has now been discovered which provides these olefins in useful quantities.

SUMMARY OF THE INVENTION

In accordance with the present invention, there is provided a process for making $C_5$ to $C_{18}$ straight chain α-olefins comprising:

A. reacting an olefinic reactant comprising a $C_5$ to $C_{18}$ straight chain internal olefin or mixture of $C_5$ to $C_{18}$ straight chain α-olefins and $C_5$ to $C_{18}$ straight chain internal olefins with an electrophilic compound containing reactive hydrogen under conditions which permit the electrophilic compound containing reactive hydrogen to add to carbon-carbon double bonds; and B. cracking the product of step A to produce a mixture of $C_5$ to $C_{18}$ straight chain α-olefins and $C_5$ to $C_{18}$ straight chain internal olefins containing a quantity of $C_5$ to $C_{18}$ straight chain α-olefins greater than that in the olefinic reactant employed in step A.

In accordance with the present invention, there is also provided a process for making $C_5$ to $C_{18}$ straight chain α-olefins comprising:

A. reacting an olefinic reactant comprising a $C_5$ to $C_{18}$ straight chain internal olefin or mixture of $C_5$ to $C_{18}$ straight chain α-olefins and $C_5$ to $C_{18}$ straight chain internal olefins with an electrophilic compound containing reactive hydrogen under conditions which permit said electrophilic compound to add to carbon-carbon double bonds, said electrophilic compound being hydrolyzable to an alcohol after addition to the carbon-carbon double bond;

B. hydrolyzing the product of step A to reduce the product of step A to a mixture of alcohols; and C. cracking the product of step B to produce a mixture of $C_5$ to $C_{18}$ straight chain α-olefins and $C_5$ to $C_{18}$ straight chain internal olefins containing a quantity of $C_5$ to $C_{18}$ straight chain α-olefins greater than that in the olefinic reactant employed in step A.

The present invention further provides a process for making $C_5$ to $C_{18}$ straight chain α-olefins comprising:

A. reacting an olefinic reactant comprising a $C_5$ to $C_{18}$ straight chain internal olefin or mixture of $C_5$ to $C_{18}$ straight chain α-olefins and $C_5$ to $C_{18}$ straight chain internal olefins with an electrophilic reactant selected from the group consisting of water and a hydrolyzable electrophilic compound containing reactive hydrogen under conditions which permit said electrophilic reactant to add to carbon-carbon double bonds;

B. when the electrophilic reactant employed in step A is a hydrolyzable electrophilic compound containing reactive hydrogen, hydrolyzing the product of step A to form alcohols;

C. converting the alcohols produced to alkyl xanthates; and

D. cracking the product of step C to produce a mixture of $C_5$ to $C_{18}$ straight chain α-olefins and $C_5$ to $C_{18}$ straight chain internal olefins containing a quantity of $C_5$ to $C_{18}$ straight chain α-olefins greater than that in the olefinic reactant employed in step A.

DETAILED DESCRIPTION OF PREFERRED EMBODIMENTS

The starting material employed in the processes of the present invention may be either a $C_5$ to $C_{18}$ straight chain internal olefin or a mixture of $C_5$ to $C_{18}$ straight chain α-olefins and $C_5$ to $C_{18}$ straight chain internal olefins (hereafter referred to simply as the "$C_5$ to $C_{18}$ straight chain olefin reactant"). Typically, the starting material will be a mixture of $C_5$ to $C_{18}$ straight chain o-olefins and $C_5$ to $C_{18}$ straight chain internal olefin isomers (i.e., the position of the double bond may not be the same in each molecule), since such mixtures are readily available from commercial processes.

The source of the starting mixture is not critical. It could come from various cracking operations such as fluid catalytic cracking or steam cracking. A particularly suitable source is from the dehydrogenation or chlorination/dehydrochlorination of n-paraffins. Mixtures of olefin dimers, such as those produced by the nickel catalyzed dimerization of olefins, are also suitable as starting materials.

The $C_5$ to $C_{18}$ straight chain olefin reactant is reacted with an electrophilic compound containing reactive hydrogen. Examples of suitable electrophilic compounds containing reactive hydrogen include, but are not limited to, water, sulfuric acid, and carboxylic acids, such as formic acid, acetic acid, trimethylacetic acid, and dimethylbutyric acids. The electrophilic compound containing reactive hydrogen is reacted with the $C_5$ to $C_{18}$ straight chain olefin reactant under conditions which permit it to add to the carbon-carbon double bond in the $C_5$ to $C_{18}$ straight chain olefins. By way of example, when the $C_5$ to $C_{18}$ straight chain olefin reactant is a mixture of n-hexenes, e.g., a mixture of 1-, 2- and 3-hexene, the resulting reaction product comprises a mixture of 2- and 3-hexyl isomers

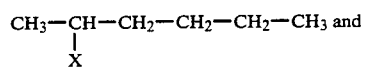

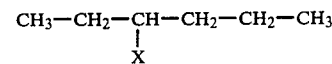

where X is the negative group (e.g., —OH, —OOCCH$_3$ or HSO$_4$—) from the electrophilic compound containing reactive hydrogen.

The conditions for the addition of the electrophilic compound to the olefins are well known in the art. Generally, acid catalysis is useful. This can often be provided by the electrophilic compound itself.

The electrophilic compounds containing reactive hydrogen useful in this invention fall into two general categories. The first category comprises compounds which, after they have added to the double bonds in the $C_5$ to $C_{18}$ straight chain olefin reactant, can be removed directly by cracking. Compounds which fall into this category include water and carboxylic acids, such as formic acid, acetic acid, trimethylacetic acid, and dimethylbutyric acids. (In some cases, it may be desirable, though not necessary, to hydrolyze the electrophilic compounds in this first category, such as the carboxylic acids, to alcohols prior to cracking). The second category of electrophilic compounds containing reactive hydrogens comprises compounds which add to the double bonds in the $C_5$ to $C_{18}$ straight chain olefin reactant, but which are not readily removed from the resulting product by cracking, e.g., sulfuric acid. When this second category of compounds is used, the product is subjected to an intermediate step, such as hydrolysis, to convert the negative group from the electrophilic compound containing reactive hydrogen (i.e., X in the above formulas) to a group, such as hydroxyl, which can be readily removed by cracking.

When the electrophilic compound containing reactive hydrogen employed is water, the isomers produced will contain hydroxyl groups in the 2 and 3+ positions, i.e., the product will contain 2-alcohol and other secondary alcohols at the 3 and farther internal positions. Also, some of the electrophilic compounds containing reactive hydrogen which are useful in this invention can be hydrolyzed to hydroxyl after addition to the double bond. These alcohols can be converted to xanthate groups, which can then be removed via cracking. This conversion of alcohol to xanthate can be accomplished by reacting the alcohol with carbon disulfide (CS$_2$) in the presence of base (e.g., NaOH), followed by alkylation with, e.g., methyl iodide.

The starting materials used in the practice of the present invention comprise, at least in part, $C_5$ to $C_{18}$ straight chain internal olefins. These internal olefins may have their double bond at various positions on the chain. The starting materials (feed) may consist of olefins having the same carbon number or a mixture of olefins of different carbon number in the $C_5$ to $C_{18}$ range Ideally, the starting material will contain a significant amount of internal olefin which has the double bond in the 2 position, i.e., between the second and third carbon atoms in the chain. It is these 2-olefins which ultimately yield α-olefins. Should the starting material not contain a significant amount of 2-olefin, it will be necessary to react the starting material with an electrophilic compound containing reactive hydrogen, crack the resulting product to a mixture of olefins, and repeat this procedure until the resulting mixture of olefins does contain a significant amount of 2-olefin. Reaction of this 2-olefin with the electrophilic compound containing reactive hydrogen will produce some $C_5$ to $C_{18}$ straight chain saturated compounds having a group in the 2 position which is removable by cracking. It may be desirable to separate this 2-isomer from the reaction product prior to the cracking step.

Once the product produced by reaction of the $C_5$ to $C_{18}$ straight chain olefin reactant with the electrophilic compound containing reactive hydrogen contains a group in the 2 position which is readily removed by cracking, that product is cracked to produce a significantly higher quantity of $C_5$ to $C_{18}$ straight chain α-olefin than was present in the $C_5$ to $C_{18}$ straight chain olefin reactant used as the starting material. It is desirable to separate those compounds having the group in the 2 position from the reaction product prior to cracking, so that only those compounds are cracked. By separating these compounds in this way, the concentration of α-olefin in the product of the cracking procedure will be maximized.

Depending upon the particular readily removable group which is present, removal of the group may be accomplished by simple thermal cracking or by a cracking procedure which utilizes a catalyst. For example, when acetic acid is used as the electrophilic compound containing reactive hydrogen, thermal cracking may be used. When water is used as the electrophilic compound containing reactive hydrogen, the resulting products are alcohols. The cracking of these alcohols is preferably conducted in the presence of a mildly basic metal oxide catalyst. Water is removed from each molecule to produce a mixture of $C_5$ to $C_{18}$ straight chain olefin isomers which has a quantity of $C_5$ to $C_{18}$ straight chain α-olefins in it which is greater than the quantity of $C_5$ to $C_{18}$ straight chain α-olefins present in the $C_5$ to $C_{18}$ straight chain olefin reactant used as the starting material.

The materials useful as cracking catalysts should not be acidic or strongly basic. Acidic catalysts can isomerize the α-olefin produced to internal olefins, which is undesirable. If a strongly basic catalyst is used, appreciable dehydrogenation of the alcohol could occur, which is undesirable. Thus, suitable catalysts are mildly basic metal oxides which do not cause appreciable dehydrogenation of the alcohol and which exhibit selectivity for the production of α-olefins. While not specific to the production of 1-hexene, this general type of catalyst is discussed in an article by Burtron H. Davis entitled "Alcohol Conversion Selectivity as a Measure of the Base Strength of Metal Oxide Catalysts" in Che et al., *Adsorption and Catalysis on Oxide Surfaces* (1985); which article is incorporated by reference herein in its entirety. Examples of mildly basic metal oxides suitable as catalysts in this invention include the oxides of Y, Zr, La, In, Ce, Pr, Nd, Sm, Eu, Dy, Ho, Yb and Th.

It has been found that hydrous zirconium oxide prepared by a particular technique is an especially suitable catalyst. This catalyst is prepared by precipitating/digesting soluble $ZrO(NO_3)_2$ at high pH above room temperature (e.g., about 50°–75° C.), washing the resulting product thoroughly with both aqueous ammonia and water and drying exhaustively (e.g., at 80° C. or higher under vacuum for at least 16 hours). Before use, the catalyst is calcined at about 350°–650° C. This catalyst provides excellent conversion of 2-hexanol to olefin as well as excellent selectivity for α-olefin in the product.

When the $C_5$ to $C_{18}$ straight chain olefin reactant is a mixture of $C_6$ olefin isomers, the above-described process can be depicted by the following general reaction scheme. This general reaction scheme is illustrative only and is not intended to limit the present invention in any way.

STEP 1

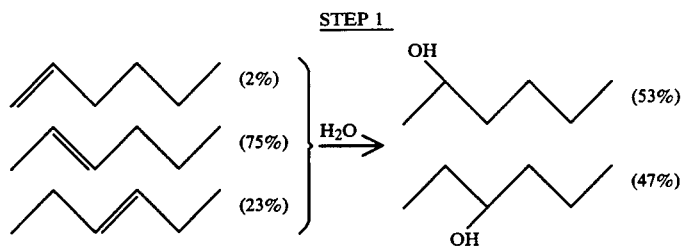

In the above Step 1, the percentages in parentheses refer to the relative amounts of 1-, 2- and 3-hexene, i.e., the weight percentages of 1-, 2- and 3-hexene based on the total weight of 1-, 2- and 3-hexene.

The yield of 2-hydroxyhexane (which ultimately can yield 1-hexene) in Step 1 (53 wt. % of the total product) is not substantially higher than the yield which would be expected for random addition of the water to the double bonds, i.e., about 50% of the alcohols produced would be expected to be 2-hydroxyhexane if random addition occurred. However, it has been found that the amount of 2-hydroxyhexane in this product can be increased significantly above this random level by using an electrophilic compound containing reactive hydrogen other than water. For instance, if acetic acid is used, the product contains about 63% of the 2-isomer and 37% of the 3-isomer. Using sulfuric acid as the electrophilic compound containing reactive hydrogen yields a product containing about 73% of the 2-isomer and 27% of the 3-isomer. The use of "bulky" acids, such as trimethylacetic acid or dimethylbutyric acids, should likewise increase the amount of 2-isomer in the product.

The product of Step 1 can next be "cracked" to a mixture of n-hexenes. The resulting mixture contains a quantity of 1-hexene substantially higher than the quantity present in the starting material used in Step 1.

STEP 2

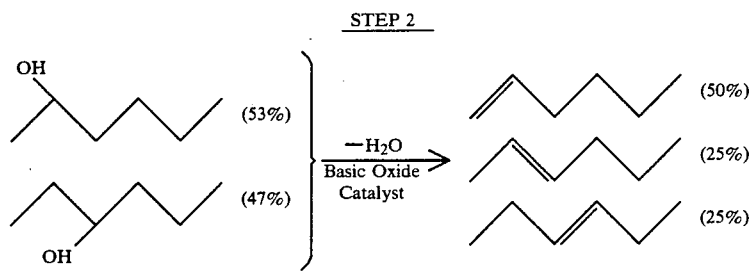

The desired product from the above reaction sequence is, of course, 1-hexene. However, it is not necessary that the 1-hexene be separated from the 2- and 3-hexene in order for it to be useful. For example, the mixture of 1-, 2- and 3-hexene can be used as a starting material for the copolymerization of 1-hexene and ethylene. Since 2- and 3-hexene will not react to copolymerize with the ethylene, they act simply as an inert diluent which can be recovered following the copolymerization of the 1-hexene and ethylene. Thus, the copolymerization also serves as a means of separating the 2- and 3-hexene from the 1-hexene.

Should it be desirable to separate the 1-hexene from the mixture of 1-, 2- and 3-hexene prior to its use, this can be accomplished by techniques such as distillation or adsorption, which are well known in the art.

The processes of the present invention may be conducted either as a batch process or in a continuous manner. It is generally preferable to conduct the process in a continuous manner. The product of the cracking step will generally contain some quantity of $C_5$ to $C_{18}$ straight chain internal olefins, and possibly some compounds which were not cracked and still contain the electrophilic group of the electrophilic compound containing reactive hydrogen (e.g., hydroxyls). Thus, the processes of this invention are advantageously conducted by recovering the desired product, the $C_5$ to $C_{18}$ straight chain α-olefin, from the product of the cracking step, and recycling any remaining internal olefins and uncracked compounds to be used as a portion of the feed for the reaction with the electrophilic compound containing active hydrogen. This may be accomplished by recycling these compounds to a point in the process where they will become part of the original starting material, i.e., to a point prior to reaction with the electrophilic compound containing reactive hydrogen. In this way the amount of α-olefin produced from a given $C_5$ to $C_{18}$ straight chain olefin reactant is maximized.

One of the principle advantages of the present invention is that it provides a process whereby $C_5$ to $C_{18}$ straight chain α-olefins can be produced in commercially acceptable amounts. In effect, the process of this invention starts with a reactant which is low in $C_5$ to $C_{18}$ straight chain α-olefins and raises the quantity of such α-olefins in the reactant by converting some of the $C_5$ to $C_{18}$ straight chain internal olefins in the reactant to the corresponding α-olefin. For example, a typical mixture of n-hexenes used as the starting material may contain about 75% 2-hexene, about 23% 3-hexene and only about 2% 1-hexene, all percentages being by weight based on the total weight of the 1-, 2- and 3-hexene. By practicing the present invention, the amount of 1-hexene can be raised to about 50% or higher.

The present invention is further illustrated by the following examples in which all percentages are by weight unless otherwise stated.

EXAMPLE 1

This example illustrates the hydration of n-hexenes using sulfuric acid.

50 Grams of a mixture containing 1% 1-hexene, 71% 2-hexene and 28% 3-hexene was added to 93 grams of 78% sulfuric acid at 15° C. over 10 minutes while stirring and cooling. Then 60 grams of concentrated (96–97%) sulfuric acid was added over 15 minutes while keeping the temperature of the mixture at 15° C. The resulting mixture was digested at 24° C. for 1 hour. Then 288 grams of water was added at 15° C. and the intermediate sulfates which formed were hydrolyzed by heating at 80° C. for 3 hours. The resulting product contained about 70% 2-hexanol and 30% 3-hexanol. The results of this experiment and three other similar experiments are summarized below in Table I.

TABLE I n-HEXENE HYDRATION

| Run No. | Olefin Addition[1] | | $H_2SO_4$ Addition[2] | | Digestion | | Water Addition[3] Temp. °C. | Hydrolysis | | Products[4] | |
|---|---|---|---|---|---|---|---|---|---|---|---|
| | Temp. °C. | Time, Min. | Temp. °C. | Time, Min. | Temp. °C. | Time, Min. | | Temp. °C. | Time, Min. | Color, Gardner | GC Percent 2-Hexanol in Hexanols |
| 1 | 15 | 10 | 15 | 15 | 24 | 60 | 15 | 80 | 180 | 7 | 71 |
| 2 | 30 | 10 | 30 | 15 | 30 | 60 | 30 | 80 | 180 | 7.5 | 72 |
| 3 | 5 | 10 | 5 | 15 | 5 | 120 | 15 | 80 | 180 | 4 | 74 |
| 4 | 15 | 45 | 15 | 60 | 24 | 60 | 15 | 80 | 180 | 4.5 | 73 |

[1] 50 g (0.595 moles) n-hexene added to 93 g of 78 $H_2SO_4$ (0.74 moles)
[2] 60 g (0.59 moles) conc. $H_2SO_4$
[3] 288 g water
[4] Organic layer washed with base and dried.

The hydration procedure described in this example can be used in the present invention as Step 1 in the above-described general reaction scheme.

EXAMPLE 2

A mixture of n-hexenes was prepared containing 92.4% n-hexenes and 7.6% branched hexenes. This mixture was hydrated by a procedure similar to that of Example 1 except that the starting sulfuric acid strength was about 77% and the stronger acid (137 grams) added subsequently was only about 82%. The conversion (about 75%) and alcohol isomer distribution (73% 2-hexanol and 27% 3-hexanol) were about the same as in Example 1. The minor amount of branched hexenes in the feed mostly formed oligomers which were easily separated by distillation.

The hydrated hexenes prepared above were distilled. The results are shown in Table II below. The 2- and 3-hexanols were partially separated with the last cuts being up to about 97% 2-hexanol.

TABLE II

DISTILLATION OF HEXANOLS FROM DIMATE[5]

| Cut | Boiling Point, °C. | Composition, GC Area % | | | | | |
|---|---|---|---|---|---|---|---|
| | | n-Hexene | "Branched Hexene" | "Branched Hexanol" | 3-Hexanol | 2-Hexanol | Oligomer |
| 1 | 62–64 | 90.4 | 8.2 | — | 0.5 | 0.9 | — |
| 4 | 68–70 | 91.2 | 6.4 | 0.1 | 0.8 | 1.5 | — |
| 8 | 138 | — | — | 1.2 | 43.6 | 55.2 | — |
| 13 | 139– | — | — | 0.2 | 41.4 | 58.2 | — |
| 18 | 139+ | — | — | — | 38 | 62 | — |
| 20–36 | 139–140.5 | | | — | 26.9 | 73.1 | — |
| 37–43 | 140.5–141 | | | | 9.7 | 90.3 | — |
| 46 | 197–199 | | | | 0.1 | 1.2 | 98.7 ($C_{12}$) |
| Bottoms | 253+ | | | | | | 100 ($C_{18}+$) |

[5] 3-Ft Spinning Band, Atm. Pressure, 20/1 reflux ratio, 2% Cuts

As with the procedure described in Example 1, the hydration procedure described in this example can be used in the practice of the present invention as Step 1 in the above-described general reaction scheme.

EXAMPLE 3

This example illustrates the dehydration of hexanols.

A wide range of catalysts was tested to identify catalysts that would produce 1-hexene in high selectivities from the dehydration of 2-hexanol. One catalyst which performed well was a zirconia powder sold by Magnesium Elektron Inc. known as "SC101". This powder was pelletized and crushed to 10–30 mesh particles. Four grams were packed in a 0.5 in. diameter quartz tube and calcined in nitrogen at 550° C. for 4 hours. The feed alcohol was passed at 0.5 ml/hr over the catalyst at 300° C. in a nitrogen flow of 3 ml/min. Two blends of 2- and 3-hexanols from Table II (cuts 20–36 and cuts 37–43) were dehydrated by this procedure. In both cases the 2-hexanol component of the blend was about 40 to 60% converted to hexenes and a small amount of hexanones. Selectivity to olefin was about 94% and 1-hexene selectivity was about 75%. 1-Hexene can be recovered in pure form from the resulting product by careful fractional distillation.

The procedure described in this example can be used in the practice of this invention as Step 2 in the above-described general reaction scheme.

What is claimed is:

1. A process for making $C_5$ to $C_{18}$ straight chain α-olefins comprising:
    A. reacting an olefinic reactant comprising a $C_5$ to $C_{18}$ straight chain internal olefin or mixture of $C_5$ to $C_{18}$ straight chain α-olefins and $C_5$ to $C_{18}$ straight chain internal olefins with an electrophilic compound containing reactive hydrogen under conditions which permit the electrophilic compound containing reactive hydrogen to add to carbon-carbon double bonds; and
    B. cracking the product of step A to produce a mixture of $C_5$ to $C_{18}$ straight chain α-olefins and $C_5$ to $C_{18}$ straight chain internal olefins containing a quantity of $C_5$ to $C_{18}$ straight chain α-olefins greater than that in the olefinic reactant employed in step A.

2. The process of claim 1 wherein the electrophilic compound is selected from the group consisting of water and carboxylic acids.

3. The process of claim 1 further comprising separating the $C_5$ to $C_{18}$ straight chain α-olefin from the product of the cracking step and recycling the remainder of said product to form a portion of the material used to react with the electrophilic compound containing reactive hydrogen.

4. A process for making $C_5$ to $C_{18}$ straight chain α-olefins comprising:
    A. reacting an olefinic reactant comprising a $C_5$ to $C_{18}$ straight chain internal or mixture of $C_5$ to $C_{18}$ straight chain α-olefins and $C_5$ to $C_{18}$ straight chain internal olefins with an electrophilic compound containing reactive hydrogen under conditions which permit said electrophilic compound to add to carbon-carbon double bonds, said electrophilic compound being hydrolyzable to an alcohol after addition to the carbon-carbon double bond;
    B. hydrolyzing the product of step A to reduce the product of step A to a mixture of alcohols; and
    C. cracking the product of step B to produce a mixture of $C_5$ to $C_{18}$ straight chain α-olefins and $C_5$ to $C_{18}$ straight chain internal olefins containing a quantity of $C_5$ to $C_{18}$ straight chain α-olefins greater than that in the olefinic reactant employed in step A.

5. The process of claim 4 wherein the electrophilic compound is sulfuric acid or a carboxylic acid.

6. The process of claim 4 further comprising separating the $C_5$ to $C_{18}$ straight chain α-olefin from the product of the cracking step and recycling the remainder of said product to form a portion of the material used to react with the electrophilic compound.

7. A process for making $C_5$ to $C_{18}$ straight chain α-olefins comprising:
    A. reacting an olefinic reactant comprising a $C_5$ to $C_{18}$ straight chain internal or mixture of $C_5$ to $C_{18}$ straight chain α-olefins and $C_5$ to $C_{18}$ straight chain internal olefins with an electrophilic reactant selected from the group consisting of water and a hydrolyzable electrophilic compound containing reactive hydrogen under conditions which permit said reactant to add to carbon-carbon double bonds;
    B. when the electrophilic reactant employed in step A is a hydrolyzable electrophilic compound containing reactive hydrogen, hydrolyzing the product of step A to form alcohols;

C. converting the alcohols produced to alkyl xanthates; and

D. cracking the product of step C to produce a mixture of $C_5$ to $C_{18}$ straight chain α-olefins and $C_5$ to $C_{18}$ straight chain internal olefins containing a quantity of $C_5$ to $C_{18}$ straight chain α-olefins greater than that in the olefinic reactant employed in step A.

8. The process of claim 7 wherein the electrophilic reactant in step A is selected from water, sulfuric acid, and carboxylic acids.

9. The process of claim 7 further comprising separating the $C_5$ to $C_{18}$ straight chain α-olefins from the product of the cracking step and recycling the remainder of said product to form a portion of the material used to react with the electrophilic reactant.

10. The process of claim 1, 4 or 7 wherein the olefinic reactant is a mixture of n-hexenes.

11. The process of claim 1, 2, 3, 4, or 6 wherein the cracking is conducted in the presence of a mildly basic metal oxide catalyst capable of selectively producing α-olefins.

* * * * *